US012667272B2

(12) United States Patent
Grbic et al.

(10) Patent No.: US 12,667,272 B2
(45) Date of Patent: Jun. 30, 2026

(54) AI POWERED WHOLE BODY MRI SCREENING

(71) Applicant: Siemens Healthineers AG, Forchheim (DE)

(72) Inventors: Sasa Grbic, Plainsboro, NJ (US); Dorin Comaniciu, Princeton, NJ (US)

(73) Assignee: Siemens Healthineers AG, Forchheim (DE)

( * ) Notice: Subject to any disclaimer, the term of this patent is extended or adjusted under 35 U.S.C. 154(b) by 122 days.

(21) Appl. No.: 18/432,133

(22) Filed: Feb. 5, 2024

(65) Prior Publication Data

US 2025/0248616 A1      Aug. 7, 2025

(51) Int. Cl.
| | |
|---|---|
| *A61B 5/00* | (2006.01) |
| *A61B 5/055* | (2006.01) |
| *G01R 33/54* | (2006.01) |
| *G06T 7/00* | (2017.01) |
| *G16H 15/00* | (2018.01) |
| *G16H 30/40* | (2018.01) |

(52) U.S. Cl.
CPC ............ *A61B 5/055* (2013.01); *A61B 5/7267* (2013.01); *G01R 33/543* (2013.01); *G06T 7/0012* (2013.01); *G16H 15/00* (2018.01); *G16H 30/40* (2018.01); *G06T 2207/10016* (2013.01); *G06T 2207/10088* (2013.01); *G06T 2207/20081* (2013.01); *G06T 2207/20084* (2013.01); *G06T 2207/30096* (2013.01); *G06T 2207/30101* (2013.01)

(58) Field of Classification Search
CPC ...................................................... A61B 5/055
See application file for complete search history.

(56) References Cited

U.S. PATENT DOCUMENTS

| | | | |
|---|---|---|---|
| 2019/0228857 A1* | 7/2019 | Lin | G06N 20/00 |
| 2019/0320934 A1* | 10/2019 | Odry | G01R 33/54 |

OTHER PUBLICATIONS

Amin, Mahul B. et al., The Eighth Edition AJCC Cancer Staging Manual: Continuing to build a bridge from a population-based to a more "personalized" approach to cancer staging; CA Cancer J Clin.; 2017 vol. 67; pp. 93-99.
Atilla P. Kiraly et al.; Deep Convolutional Encoder-Decoders for Prostate Cancer Detection and Classification; M. Descoteaux et al. (Eds.): MICCAI 2017, pp. 489-497, 2017.
LiverLab; Siemens Medical Solutions USA, Inc.; 2024; pp. 1-5.
Syngo Inline VF; Siemens Medical Solutions USA, Inc.; 2024; pp. 1-5.

* cited by examiner

*Primary Examiner* — Joseph M Santos Rodriguez

(57) ABSTRACT

Systems and methods that leverage the power of artificial intelligence (AI) to enhance the process of whole-body MRI scanning. AI models optimize the acquisition protocol, resulting in shorter and more patient-friendly scan durations. Furthermore, AI models aid in the automatic interpretation of the imaging data, highlighting potential areas of concern and streamlining the diagnostic process.

9 Claims, 5 Drawing Sheets

AI POWERED WHOLE BODY MRI SCREENING

FIELD

This disclosure relates to whole body MRI (Magnetic Resonance Imaging) screening.

BACKGROUND

One of the significant challenges in medicine today is the late detection of diseases. In many cases diseases are detected often when they have progressed to more severe stages and are harder to treat or manage. For example, detecting lung cancer in early stages improves the 5 year survival from approximately 18% (if detected late) to 73% (if detected early). This delay is attributed to multiple factors, including non-specific symptoms and the absence of a comprehensive screening method that can detect diseases at an early stage across different body systems. Whole-body magnetic resonance imaging (WB-MRI) has become established for the management of specific patients with multiple epithelial and non-epithelial cancers, and recently its use has been extended to early cancer detection in subjects with cancer predisposition syndromes.

However, WB-MRI has immense potential as a screening and early diagnosis tool, for example to detect cancers in the general population. The premise being that earlier detection and appropriate targeted interventions can modify the risk of disease development and so promote precision health. However, the widespread use of WB-MRI for full-body screening has been limited due to the long acquisition time and the need for specialized interpretation by a specialist, for example a radiologist. In addition, the large amount of imaging that is acquired during WB-MRI has typically led it to be an extremely costly exam.

SUMMARY

By way of introduction, the preferred embodiments described below include methods, systems, instructions, and computer readable media for whole body MRI screening using AI models.

In a first aspect, a method for Whole Body MRI Screening using AI powered models, the method comprising: determining, by a first AI model, a personalized set of MR sequences for a patient based on initial images and available clinical data; performing whole body MRI screening for the patient comprising the personalized set of MR sequences; and interpreting the results of the whole body MRI screening using one or more second AI models.

In an embodiment, determining comprises: tailoring personalized set of MR sequences based on the patent's age, risk factors, and prior medical history. The method may further include adjusting the whole body MRI screening based on real-time analysis of real-time results of one or more of the personalized set of MR sequences.

In an embodiment, interpreting comprises: identifying one or more areas of potential concern for the patient, wherein the one or more areas related to a tumor, vascular anomaly, or sign of degenerative diseases. Interpreting may comprise comparing results of the personalized set of MR sequences with prior MRIs, CTs, or other images from the patient's history; and identifying any changes or developments.

The method may further include generating a report based on the interpreted results. The report may include simple language and simple visuals for the patient. The method may further include identifying one or more areas of potential concern for the patient based on results from an initial sequence of the personalized set of MR sequences, wherein the one or more areas related to a tumor, vascular anomaly, or sign of degenerative diseases; and selecting a new sequence not included in the personalized set of MR sequences based on the identification.

In an embodiment, the first AI model and/or the one or more second AI models comprise machine trained neural networks. The one or more second AI models may comprise at least one machine trained network trained for segmenting image data for a specific region of the patient. The at least one machine trained network may include a machine trained segmentation network.

In a second aspect, a system for whole body MR screening, the system comprising: a first AI model configured to select a personalized set of MR sequences for a patient based on initial images and available clinical data; a MR scanner configured to perform the personalized set of MR sequences; a second AI model configured to analyze data from a first sequence of the personalized set of MR sequences; and a third AI model configured to interpret the analysis of the second AI model and generate a diagnostic report.

The first AI model may be configured to tailor the personalized set of MR sequences based on the patent's age, risk factors, and prior medical history. The personalized set of MR sequences may be adjusted based on the analysis of the second AI model. The second AI model may be configured to identify one or more areas of potential concern for the patient, wherein the one or more areas related to a tumor, vascular anomaly, or sign of degenerative diseases.

The system may further include a fourth AI model configured to analyze data from a second sequence of the personalized set of MR sequences, wherein the third AI model is further configured to interpret the analysis of the fourth AI model and generate the diagnostic report based at least partially thereon.

The third AI model may be configured to compare results of the personalized set of MR sequences with prior MRIs, CTs, or other images from the patient's history to generate the diagnostic report.

The first AI model, second AI model, and third AI model may comprise machine trained neural networks configured for each respective task.

In a third aspect, a method for whole body MR screening, the method comprising: determining, by a first AI model, a personalized set of MR sequences for a patient based on initial images and available clinical data; performing, by a MR scanning system, a first sequence of the personalized set of MR sequences; analyzing, by a second AI model, results from the first sequence, wherein analyzing comprises at least identifying an anomaly in the results; selecting, by a third AI model, an additional sequence to be performed based on the analysis of the second AI model; performing, by the MR scanning system, the additional sequence; interpreting, by a fourth AI model, the results of the additional sequence; and generating, by a fifth AI model, a report based on at least the results of the additional sequence.

Any one or more of the aspects described above may be used alone or in combination. These and other aspects, features and advantages will become apparent from the following detailed description of preferred embodiments, which is to be read in connection with the accompanying drawings. The present invention is defined by the following claims, and nothing in this section should be taken as a limitation on those claims. Further aspects and advantages of the invention are discussed below in conjunction with the preferred embodiments and may be later claimed independently or in combination.

DETAILED DESCRIPTION

Figure 1:
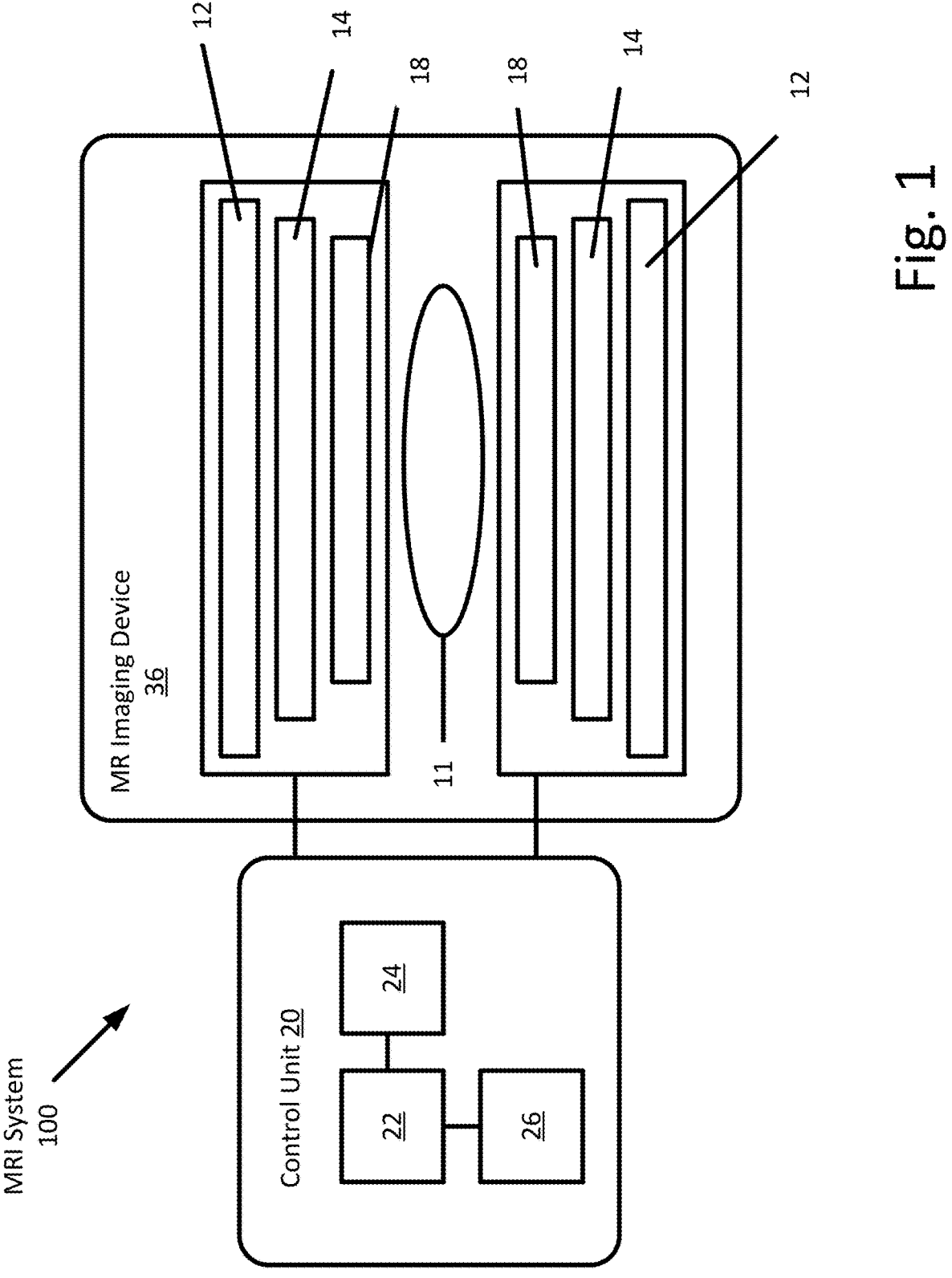
FIG. 1 depicts an MR system 100 for Whole Body MRI screening according to an embodiment.

Embodiments described herein provide systems and methods for Whole Body MRI screening using AI powered models. An imaging modality without radiation such as MRI has the potential to be used in early screening procedures but due to the long exam times and the requirement for a read by a radiologist, this service is cost and resource prohibitive. There is a pressing need for an efficient and comprehensive screening method that will improve survival rates on a population level. By leveraging the power of AI, whole-body MRI can become the yearly screening exam that serves as a valuable tool for early disease detection.

MRI protocols and procedures for whole body MRI screening may include a standard protocols. While different physicians may order different sequences to be performed under different protocols or procedures, the use of standardized protocols leads to inefficiencies. Additional scans are performed when not needed (and not used in the eventual diagnosis or treatment). Scans that might be useful may not be performed, leading to a delayed diagnosis or treatment. In addition, the amount of data acquired during a whole body MRI screening can overwhelm an operator/radiologist. Upwards of several hundred or thousands of images/volumes may be acquired that need to be interpreted. A patient may be required to come back for additional imaging procedures if an abnormality is found after the screening has finished. These inefficiencies and others make whole body MRI screening less than optimal in its current state.

The disclosed embodiments may be implemented to computationally facilitate processing of medical imaging data and consequently improving and optimizing medical diagnostics. Embodiments leverage the power of artificial intelligence (AI) to enhance the process of whole-body MRI scanning. AI optimizes the acquisition protocol, resulting in shorter and more patient-friendly scan durations. Furthermore, AI aids in the automatic interpretation of the imaging data, highlighting potential areas of concerns and thus streamlining the diagnostic process. By using an automated workflow based on AI models, errors in the scanning process are diminished and outcomes are improved. The use of an AI generated acquisition procedure is efficient in that a correct number of resources are used to acquire the needed medical images for diagnosis. The use of an automated acquisition procedure further limits errors by removing user errors and decisions from the process. The automated acquisition process not only automates image acquisition in general but also automatically tailors the process for each patient. The generated patient-specific process saves time for both the patient and any personal that reviews the images. The use of AI models in the interpretation further increases the efficiency of the process allowing for real time adjustment in the acquisition, improved diagnostics, and potentially better patient outcomes.

As used herein, artificial intelligence (AI) is the use of machine learning models to acquire medical data and uncover insights to help improve health outcomes and patient experience. The whole body MRI based screening exam described herein provides cost efficient acquisition and interpretation that is supported by AI. The reduced MRI scan time improves patient experience and increases the throughput of MRI facilities. The AI-driven insights may potentially reduce human errors and improve the reliability of diagnoses. Additionally, faster scans and reduced need for expert reviews enables a cost-efficient screening exam that leverages Whole Body MRI.

FIG. 1 depicts an MR system 100 for Whole Body MRI Screening using AI powered models. The MR system 100 includes a control unit 20 configured to determine a set of sequences for a whole body MRI screening procedure for a patient. The control unit 20 is further configured to process the MR signals and generate images of the body for analysis and/or display to an operator, for example, using a processor 22. The control unit 20 may store the MR signals and images in a memory 24. The control unit 20 may include a display 26 for presentation of images to an operator. The control unit 20 is configured to analysis the MR signals and images in order to adjust the set of sequences while the screening procedures proceeds. The control unit 20 is further configured to interpret the MR signals and images. The MR scanning system 100 for Whole Body MRI Screening is only exemplary, and a variety of MR scanning systems may be used to collect the MR data.

In the MR system 100, magnetic coils 12 create a static base or main magnetic field $B_0$ in the body of patient 11 or an object positioned on a table and imaged. Within the magnet system are gradient coils 14 for producing position dependent magnetic field gradients superimposed on the static magnetic field. Gradient coils 14, in response to gradient signals supplied thereto by a gradient and control unit 20, produce position dependent and shimmed magnetic field gradients in three orthogonal directions and generate magnetic field pulse sequences. The shimmed gradients compensate for inhomogeneity and variability in an MR imaging device magnetic field resulting from patient anatomical variation and other sources.

The control unit 20 may include a RF (radio frequency) module that provides RF pulse signals to RF coil 18. The RF coil 18 produces magnetic field pulses that rotate the spins of the protons in the imaged body of the patient 11 by ninety degrees or by one hundred and eighty degrees for so-called "spin echo" imaging, or by angles less than or equal to 90 degrees for "gradient echo" imaging. Gradient and shim coil control modules in conjunction with RF module, as directed by control unit 20, control slice-selection, phase-encoding, readout gradient magnetic fields, radio frequency transmission, and magnetic resonance signal detection, to acquire magnetic resonance signals representing planar slices of the patient 11.

In response to applied RF pulse signals, the RF coil 18 receives MR signals, e.g. signals from the excited protons within the body as the protons return to an equilibrium position established by the static and gradient magnetic fields. The MR signals are detected and processed by a detector within RF module and the control unit 20 to provide an MR dataset to a processor 22 for processing into an image. In some embodiments, the processor 22 is located in the control unit 20, in other embodiments, the processor 22 is located remotely. A two or three-dimensional k-space storage array of individual data elements in a memory 24 of the control unit 20 stores corresponding individual frequency components including an MR dataset. The k-space array of individual data elements includes a designated center, and individual data elements individually include a radius to the designated center.

A magnetic field generator (including coils 12, 14 and 18) generates a magnetic field for use in acquiring multiple individual frequency components corresponding to individual data elements in the storage array. The individual frequency components are successively acquired using a Cartesian or other spatial acquisition strategy as the multiple individual frequency components are sequentially acquired during acquisition of an MR dataset. A storage processor in the control unit 20 stores individual frequency components acquired using the magnetic field in corresponding individual data elements in the array. The row and/or column of corresponding individual data elements alternately increases and decreases as multiple sequential individual frequency components are acquired. The magnetic field generator acquires individual frequency components in an order corresponding to a sequence of substantially adjacent individual data elements in the array, and magnetic field gradient change between successively acquired frequency components is substantially minimized.

The control unit 20 may use information stored in an internal database to process the detected MR signals in a coordinated manner to generate high quality images of a selected slice(s) of the body (e.g., using an image data processor) and adjusts other parameters of the system 100. The stored information may include, for example, a predetermined pulse sequence of an imaging protocol and a magnetic field gradient and strength data as well as data indicating timing, orientation, and spatial volume of gradient magnetic fields to be applied in imaging. Alternative reconstruction processes may be used to generate images of a selected slice.

For Whole Body MRI screening, multiple different sequences may be used, including but not limited to Fastview, STIR spine sag, T1 spine sag, T1 dixon VIBE axial, DWI axial, T2 HASTIRM, T2 Haste, etc. The different sequences are used to acquire different information about different organs/parts of the patient's body.

Figure 2:
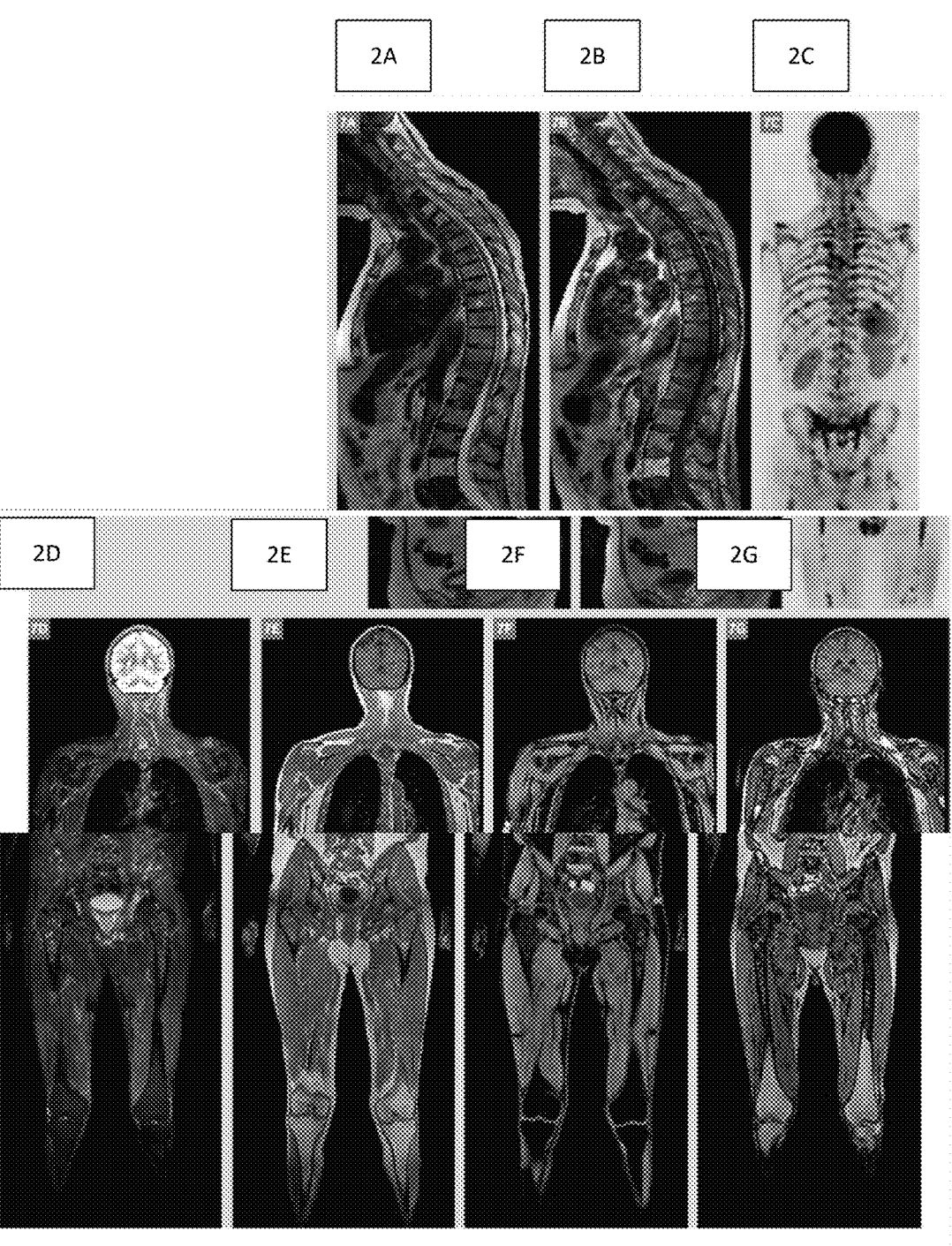
FIGS. 2A-2G depicts several examples of images from different sequences performed for whole body MRI screening according to an embodiment.

FIGS. 2A-2G depict the results from different potential sequences for a whole body MRI screening procedure. FIG. 2A depicts a sagittal T2. FIG. 2B depicts a sagittal T1. FIG. 2C depicts MIP of composed high b-value inverted transverse DWI. FIG. 2D depicts coronal TRIM. FIG. 2E depicts a coronal VIBE 'in phase' image. FIG. 2F depicts a coronal VIBE 'water' phase. FIG. 2G depicts a coronal VIBE 'out of phase' image. The MR scanning system 100 for Whole Body MRI screening is configured to select the appropriate sequences for a patient based on information for the patient such as the patient's age, risk factors, and prior medical history. A patient that has a history or proclivity towards cancer may be provided different sequences than a patient that does not. An older patient may be provided with different sequences than a younger patient. As further described below, the sequences may be adjusted based on feedback from previous sequences. The possible sequences may also be limited by either hardware (for example the type of scanner), available time, or computational resources. The following sequences are exemplary, but other sequences may be used to acquire data for different regions or body parts. The entirety of the set of sequences may be performed during a single session where the patient is positioned inside a MR scanner.

The Whole Body MRI screening imaging protocol generally includes morphological T1- and T2-weighted sequences along with DWI. T1-weighted images are usually obtained with gradient-echo (GRE) Dixon acquisitions producing in- and opposed-phase images that allow the calculation of fat-only and water-only images. T1-weighted images may be useful in the detection, characterization and response assessment of bone metastases. As an alternative, a T1-weighted 3D turbo spin echo (TSE) sequence may be performed that foregoes the discrimination of water and fat components but may result in a longer acquisition. T2-weighted images, acquired using single-shot or half-acquisition turbo spin echo (HASTE) sequences without fat suppression may be used for the evaluation of disease in organs other than bone with a good trade-off between duration and signal to noise ratio (SNR), and may be helpful in confirming the presence of spinal cord compression. Sagittal T1-weighted TSE and fat-saturated (short tau inversion recovery-STIR) T2-weighted TSE images of the whole spine may be used for the detection of vertebral metastases, fractures and spinal cord compression. A single-shot diffusion-weighted echo-planar imaging sequence may be used to detect malignant lesions characterized by high cellularity. Acquiring multiple averages of the DWI data during free-breathing is recommended in order to reduce motion artefacts and increase SNR. At least two b-values may be needed in order to calculate the corresponding apparent diffusion coefficient (ADC) map for image interpretation and disease response assessment. The use of a single diffusion encoding direction with simultaneous application of gradients from all three axes can provide higher SNR by reducing echo times. Whole body DWI requires a relatively long (10-15 minutes) acquisition time. Obtaining fewer averages of the low b-value images, that have intrinsically higher SNR, may shorten the acquisition times. Coverage of the lung and brain can be incorporated by using a single breath-hold, short echo-time GRE sequence for evaluation of lung parenchyma, and a fluid-attenuated inversion recovery TSE sequence for detection of focal brain lesions or brain oedema.

In certain sequences, contrast media may be used, for example to detect it brain metastases or meningeal disease. Depending on clinical context, sequences to evaluate specific body regions may be added to a basic Whole Body MRI Screening protocol. For example, a post-contrast T1-weighted brain scan is recommended in Li-Fraumeni syndrome (LFS). For men, axial T2-weighted and DWI sequences targeted to the prostate can be added to provide an all-in-one prostate cancer (PC) staging examination.

In an embodiment, the Whole Body MRI Screening protocols cover at least from the head to the pelvis of the patient. Depending on the patient and patient information, the system 100 may determine that less or more coverage is optimal. Alternatively, the Whole Body MRI screening acquisitions may span from the vertex to mid-thigh. The acquisition may be extended to the patient's feet when performed for diseases that frequently involve the extremities, such as neurofibromatosis, or as part of surveillance in cancer predisposition syndromes that favor soft-tissue tumors, such as LFS. The acquisition of Whole Body MRI Screening in patients affected by multiple myeloma may, instead, span from vertex to knees. In an example, evaluating the lower limbs of a patient is typically not performed for a standard/core Whole Body MRI screening protocol, as it is unlikely to increase diagnostic yields, in spite of a considerable increase in acquisition times. However, this region may be evaluated in patients who present with a higher risk of cancer in the long bones or in soft tissues, for example as determined automatically from the patient's or patient's family history. In another example, the option of acquiring morphological images in the axial or coronal plane is also based on patient information and the output of one or more AI based models that determine the appropriate sequences. The coronal plane has typically been used in WB-MRI studies when examinations were more time consuming, because it requires fewer slices acquired antero-posteriorly than axial imaging to cover the entire body volume, and thereby reduce scanning times. However, the advantages of axial studies include the possibility of matching morphological images to DWI, as well as comparing MRI with other cross-sectional imaging modalities such as CT. The coronal orientation may permit the acquisition of fewer stations and thus reduce scan time. Axial acquisition has an advantage in providing images that may be directly correlated with the conventional cross-sectional anatomy of other modalities. Slice thickness (SLT) may remain consistent across the different sequences to allow efficient image comparison and improve the readability of the examination.

The sequences may be selected and/or ordered in such a way that processing and analysis of the output data may be performed while the patient is being examined. In an embodiment, depending on the patient information, the system 100 selects initial or starting sequences that provide information that may be used as feedback to inform the subsequent sequences. Performing a first sequence may lead to the system 100 determining that a second sequence is not necessary or that a third typically not used sequence would be useful. The system 100 is configured to both select an optimal set of sequences and also adjust the set of sequences as the scan proceeds. The initial determination and adjustment may be based on one or more AI based models.

The control unit 20 is further configured to reconstruct a representation of the patient from the MR data from the different sequences and perform analysis/interpretation of the representation. As described above, the control unit 20 may further determine an initial sequence based on input patient information and adjust the sequences as the scan proceeds. The control unit 20 is configured to implement one or more AI based models that are trained/configured to input data and output a prediction/estimation/classification/segmentation/etc.

The control unit 20 includes one or more processors 22. The one or more processors 22 may include a general processor, digital signal processor, three-dimensional data processor, graphics processing unit, application specific integrated circuit, field programmable gate array, artificial intelligence processor, digital circuit, analog circuit, combinations thereof, or another now known or later developed device for reconstruction, analysis, interpretation, and implementation of one or more AI based models. The processor 22 may be a single device, a plurality of devices, or a network. For more than one device, parallel or sequential division of processing may be used. Different devices making up the processor may perform different functions, such as selecting a sequence by a first device, reconstructing by a second device, volume rendering by third device, and analysis by another device. In one embodiment, the processor 22 is a control processor or other processor of the MR scanner 100. Other processors of the MR scanner 100 or external to the MR scanner 100 may be used. The processor 22 is configured by software, firmware, and/or hardware to reconstruct. The instructions for implementing the processes, methods, and/or techniques discussed herein are provided on non-transitory computer-readable storage media or memories, such as a cache, buffer, RAM, removable media, hard drive, or other computer readable storage media. The instructions are executable by the processor or another processor. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the instructions set, storage media, processor or processing strategy and may be performed by software, hardware, integrated circuits, firmware, micro code, and the like, operating alone or in combination. In one embodiment, the instructions are stored on a removable media device for reading by local or remote systems. In other embodiments, the instructions are stored in a remote location for transfer through a computer network. In yet other embodiments, the instructions are stored within a given computer, CPU, GPU, or system. Because some of the constituent system components and method steps depicted in the accompanying figures may be implemented in software, the actual connections between the system components (or the process steps) may differ depending upon the manner in which the present embodiments are programmed.

Figure 3:
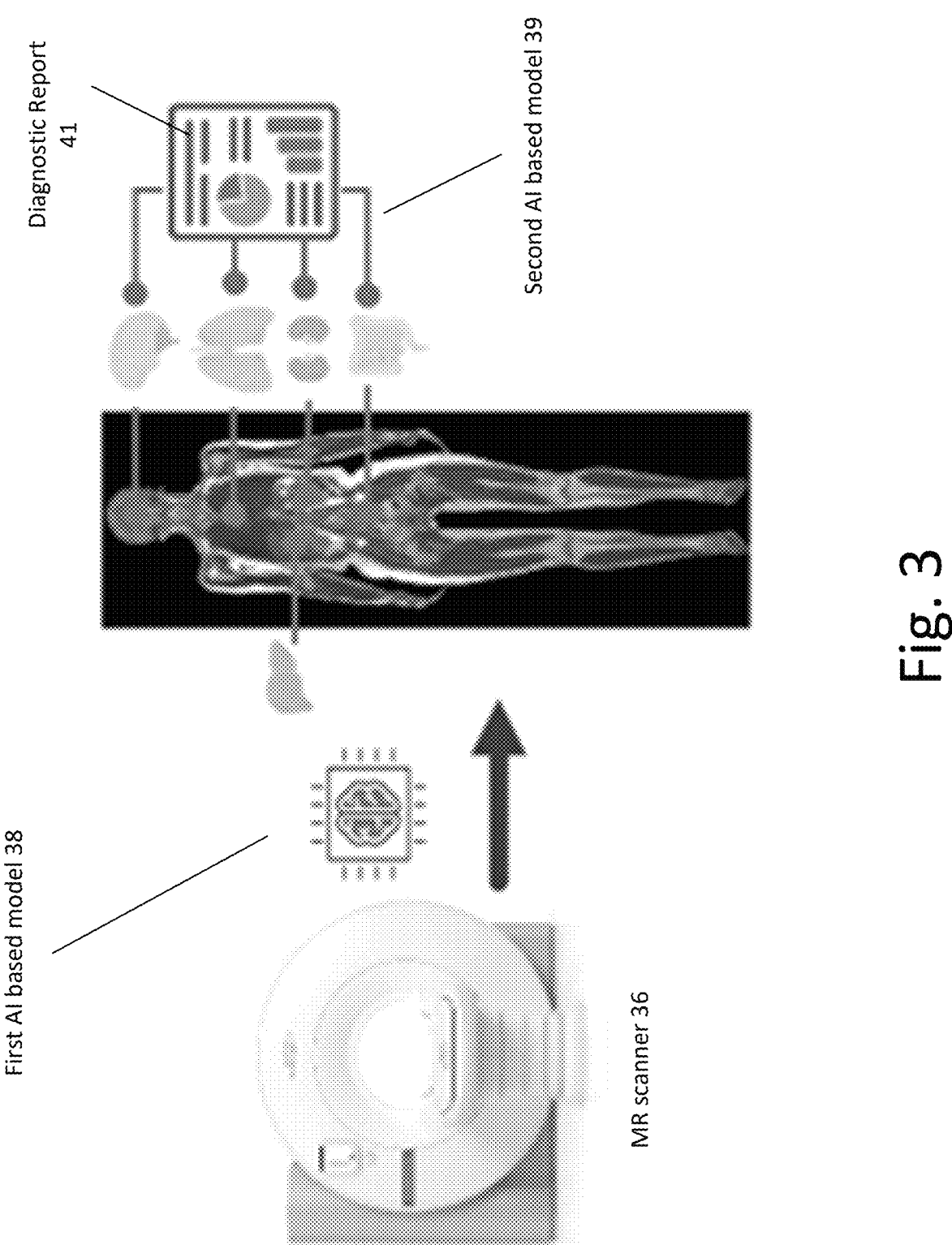
FIG. 3 depicts an example workflow for Whole Body MRI screening according to an embodiment.

The control unit 20 is configured to provide an AI-Optimized Acquisition Protocol including selecting an initial set of sequences and adjusting the sequences based on analysis of previous scans. The control unit 20 is configured to implement an AI model for Adaptive Sequencing. The AI model is trained on a large dataset of MRIs to determine an optimal sequence of scans for each patient based on initial images and available clinical data. For example, the AI model is configured to tailor the scanning protocol based on the patient's age, risk factors, and/or prior medical history. The control unit 20 is configured to provide real-time analysis of ongoing scans. The real time analysis allows the control unit 20 to adjust parameters during the procedure, ensuring optimal image quality while reducing scan time. The real time analysis and adjustment may be implemented based on one or more rules or AI models that are configured to input data from the ongoing WB-MRI procedure. FIG. 3 depicts an example of the workflow performed by the control unit 20. In FIG. 3, the MR scanner is configured to perform one or more sequences selected by the First AI based model 38. The results are interpreted by a second AI based model 39 which generates a diagnostic report. There may be multiple second AI based models 39, for example one trained specifically for each organ, region, or abnormality.

The control unit 20 is configured to reconstruct a representation of a scan region, such as a region of the patient as the WB-MRI procedure provides data for the patient. The control unit 20 may use, for example, an image processor 22 that is configured to reconstruct a representation in an object domain. The representation or object in the object domain is reconstructed from the scan data in the scan domain. The scan data is a set or frame of k-space data from a scan of the patient. The object domain is an image space and corresponds to the spatial distribution of the patient. A planar or volume representation or object is reconstructed as an image representing the patient. For example, pixels values representing tissue in an area or voxel values representing tissue distributed in a volume are generated.

The reconstruction may be a traditional approach or optimization (e.g., not machine-learning based), such as generalized auto calibrating partially parallel acquisitions. In embodiments, the reconstruction is performed, at least in part, using a machine-learned model or algorithm such as the multichannel network. The machine-learned model is formed from one or more networks and/or other machine-learned arrangements (e.g., support vector machine). For an example used herein, the machine-learned model includes one or more deep-learned neural networks included in an unrolled iterative reconstruction algorithm. A machine-learned model is used for at least part of the reconstruction, such as regularization of reconstruction. In regularization, image or object domain data is input, and image or object domain data with less artifact is output. The remaining portions or stages of the reconstruction (e.g., Fourier transform and gradients in iterative optimization) are performed using reconstruction algorithms and/or other machine-learned networks. In other embodiments, a machine-learned model is used for all the reconstruction operations (one model to input k-space data and output regularized image data) or other reconstruction operations (e.g., used for transform, gradient operation, and/or regularization). The reconstruction is of an object or image domain from projections or measurements in another domain, and the machine-learned model is used for at least part of the reconstruction.

The large number of images produced in each WB-MRI examination complicates extracting the quantitative information. The control unit 20 is configured to use AI based models to automatically analysis the output of the ongoing WB-MRI procedure. The data from the different sequences may be analyzed by different models. In an embodiment, the control unit 20 is configured to provide automated region highlighting. One or more AI models identify and highlight areas of potential concern, such as tumors, vascular anomalies, or signs of degenerative diseases. In another embodiment, the control unit 20 is configured to provide comparative analysis. The control unit 20 is configured to compare the current scans with prior MRIs, CTs, or other images from the patient's history, emphasizing any changes or developments. The control unit 20 is further configured to provide Predictive Insights. By integrating the MRI data with broader medical databases and the patient's medical history, the control unit 20 can suggest potential risks or future complications. The control unit 20 is further configured for integrated reporting: The control unit 20 generates preliminary reports, integrating its findings in a structured and easy-to-understand format, speeding up the review process for radiologists. Besides reports dedicated to a radiologist the controller is configured to generate reports that are dedicated for patients/consumers with simpler language and visuals.

For these tasks and other applications, the control unit 20 makes use of one or more trained AI models. In an embodiment, the AI models may be provided by or implemented with a neural network trained using deep learning. Each of the trained networks are defined as a plurality of sequential feature units or layers. Sequential is used to indicate the general flow of output feature values from one layer to input to a next layer. The information from the next layer is fed to a next layer, and so on until the final output. The layers may only feed forward or may be bi-directional, including some feedback to a previous layer. The nodes of each layer or unit may connect with all or only a sub-set of nodes of a previous and/or subsequent layer or unit. Skip connections may be used, such as a layer outputting to the sequentially next layer as well as other layers. Rather than pre-programming the features and trying to relate the features to attributes, the deep architecture is defined to learn the features at different levels of abstraction based on an input MR data with or without pre-processing. The features are learned to reconstruct lower level features (i.e., features at a more abstract or compressed level). For example, features for reconstructing an image are learned. For a next unit, features for reconstructing the features of the previous unit are learned, providing more abstraction. Each node of the unit represents a feature. Different units are provided for learning different features.

Various units or layers may be used, such as convolutional, pooling (e.g., max-pooling), deconvolutional, fully connected, or other types of layers. Within a unit or layer, any number of nodes is provided. For example, 100 nodes are provided. Later or subsequent units may have more, fewer, or the same number of nodes. In general, for convolution, subsequent units have more abstraction. For example, the first unit provides features from the image, such as one node or feature being a line found in the image. The next unit combines lines, so that one of the nodes is a corner. The next unit may combine features (e.g., the corner and length of lines) from a previous unit so that the node provides a shape indication. For transposed-convolution to reconstruct, the level of abstraction reverses. Each unit or layer reduces the level of abstraction or compression.

The system 100 includes an operator interface 26, formed by an input and an output. The input may be an interface, such as interfacing with a computer network, memory, database, medical image storage, or other source of input data. The input may be a user input device, such as a mouse, trackpad, keyboard, roller ball, touch pad, touch screen, or another apparatus for receiving user input. The input may receive a scan protocol, imaging protocol, or scan parameters. An individual may select the input, such as manually or physically entering a value. Previously used values or parameters may be input from the interface. Default, institution, facility, or group set levels may be input, such as from memory to the interface.

The output is a display device but may be an interface. The images, reconstructed from the scan are displayed. For example, an image of a region of the patient is displayed. A generated image of the reconstructed representation for a given patient is presented on a display of the operator interface 26. The analysis/interpretation is also displayed on the display device. The control unit 20 may be configured to generate a report for the patient that is displayed on the display device. The display is a CRT, LCD, plasma, projector, printer, or other display device. The display is configured by loading an image to a display plane or buffer. The display is configured to display the reconstructed MR image of the region of the patient. The operator interface may include form a graphical user interface (GUI) enabling user interaction with the control unit 20 and enables user modification in substantially real time.

Figure 4:
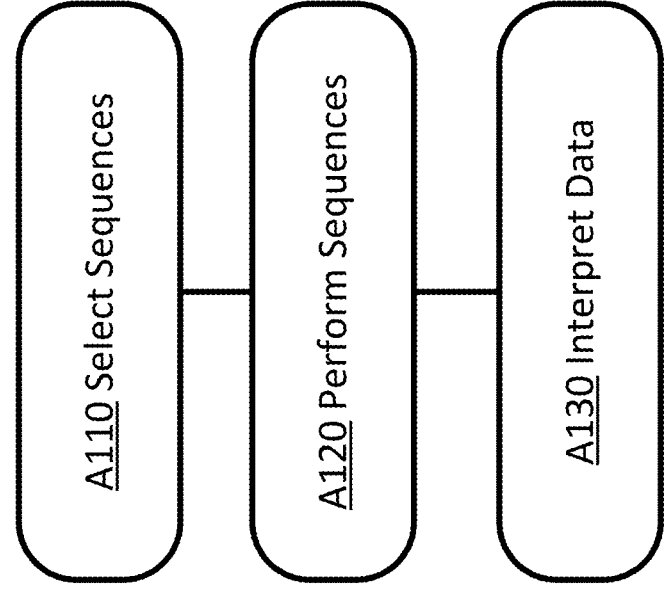
FIG. 4 depicts a method for Whole Body MRI screening according to an embodiment.

Embodiments leverage the power of artificial intelligence (AI) to enhance the process of whole-body MRI scanning. AI optimizes the acquisition protocol, resulting in shorter and more patient-friendly scan durations. Furthermore, it aids in the automatic interpretation of the imaging data, highlighting potential areas of concerns and thus streamlining the diagnostic process. FIG. 4 depicts a method for Whole Body MRI Screening using AI powered models. The acts are performed by the system of FIG. 1, 2, or 3, other systems, a workstation, a computer, and/or a server. Additional, different, or fewer acts may be provided. The acts are performed in the order shown (e.g., top to bottom) or other orders. Certain acts may be omitted or changed depending on the results of the previous acts and the status of the patient.

At act, A110, the system 100 determines an optimal sequences for a patient based on initial images and available clinical data. A machine learned model may be used to selected the optimal sequence of scans based on patient attributes. Patient information is acquired prior to the sequence being determined. The patient information may include information such as the age, sex, weight, height, etc. of the patient. The patient information may also include the medical history of the patient and/or family medical history. An AI model may be used to compare previous whole body scans of similar patients and the outcomes. The output by the system is a personalized (optimized) sequence of scans for the patient.

Different sequences may be used for different patients as different sequences may be used to acquire different data that is useful for different diagnostics. A fast view localizer may be performed first from the vertex to the knees with an axial plane in order to acquire a quick view of the patient. Subsequent scans may be adjusted or selected based on the results of the fast view localizer. Subsequent scans may include, for example, spine focused sequences including STIR and T1-weighted that are used to evaluate bone lesions and reveal any lesions threatening the spinal canal. STIR and T1 spine include a range of the whole spine in a plane that is sagittal to the patient's anatomy. The STIR may be used for fat-suppressed whole-spine imaging due to its robustness against artifacts, and ability to tailor the degree of fat suppression by varying the inversion time (T1). Whole-body sequences such as T1 Dixon, T2 HASTE, and HASTIRM may be also be used for the creation of quantitative fat-fraction images which are used to assess tumor response or progression. Previously, the creation of these images was a manual procedure involving the addition and division of image series but can now be generated inline and are composed along with the chosen Dixon contrasts. Diffusion-weighted imaging may also be used, for example to acquire liver-lesion sensitive b-value images.

T1 weighted sequences are part of almost all MRI protocols and are may provide the most 'anatomical' of images, resulting in images that most closely approximate the appearances of tissues macroscopically. The dominant signal intensities of different tissues are: fluid (e.g. urine, CSF): low signal intensity (black) muscle: intermediate signal intensity (grey) fat: high signal intensity (white) brain grey matter: intermediate signal intensity (grey) white matter: hyperintense compared to grey matter (whiteish)

The most commonly used contrast agents in MRI are gadolinium based. At the concentrations used, these agents have the effect of causing T1 signal to be increased. The contrast is injected intravenously (typically 5-15 mL) and scans are obtained a few minutes after administration. Pathological tissues (tumors, areas of inflammation/infection) demonstrate accumulation of contrast (mostly due to leaky blood vessels) and therefore appear as brighter than surrounding tissue. Often post contrast T1 sequences are also fat suppressed to make this easier to appreciate. Fat suppression (or attenuation or saturation) is a tweak performed on many T1 weighted sequences, to suppress the bright signal from fat. This is performed most commonly in two scenarios: Firstly, and most commonly, after the administration of gadolinium contrast. This has the advantage of making enhancing tissue easier to appreciate.

T2 weighted sequences are also part of almost all MRI protocols. Without modification the dominant signal intensities of different tissues are: fluid (e.g. urine, CSF): high signal intensity (white), muscle: intermediate signal intensity (grey), fat: high signal intensity (white), brain grey matter: intermediate signal intensity (grey), white matter: hypointense compared to grey matter (darkish). In many instances one wants to detect edema in soft tissues which often have significant components of fat. As such suppressing the signal from fat allows fluid, which is of high signal, to stand out. This can be achieved in a number of ways (e.g. chemical fat saturation or STIR) but the end result is the same.

Proton density (PD) images may be used for brain imaging; however, they have largely been replaced by FLAIR. PD provides excellent signal distinction between fluid, hyaline cartilage and fibrocartilage, which makes this sequence ideal in the assessment of joints. The dominant signal intensities of different tissues are: fluid (e.g. joint fluid, CSF): high signal intensity (white), muscle: intermediate signal intensity (grey), fat: high signal intensity (white), hyaline cartilage: intermediate signal intensity (grey), fibrocartilage: low signal intensity (black).

Diffusion weighted imaging assess the ease with which water molecules move around within a tissue (mostly representing fluid within the extracellular space) and gives insight into cellularity (e.g. tumors), cell swelling (e.g. ischemia) and edema. The dominant signal intensities of different tissues are: fluid (e.g. urine, CSF): no restriction to diffusion; soft tissues (muscle, solid organs, brain): intermediate diffusion; fat: little signal due to paucity of water/ Typically there are three sets of images when diffusion weighted imaging is performed: DWI, ADC and B=0 images.

Additional or fewer sequences may be used depending on the patient's medical history and the capabilities/resources of the MR scanning system 100. The system 100 may, for example, determine a set of sequences that are expected to take a predetermined time while still providing a level of diagnostic information that is appropriate for the patient. Shorter procedures may also for additional patients to be screened while still providing useful information.

At act A120, the system 100 performs whole body MRI screening for the patient including the determined optimal set of sequences. In an example implementation, the MR data is acquired using a first imaging sequence. The first imaging sequence may include at least a medium or low-resolution sequence such as fast view localizer. In an embodiment, multiple sequences may be performed. As depicted and described in FIG. 1 above, the MR data is acquired using an MR scanner. For example, gradient coils, a whole-body coil, and/or local coils generate a pulse or scan sequence in a magnetic field created by a main magnet or coil. The whole-body coil or local coils receive signals responsive to the re-orientation of molecules shifted due to the scan sequence. Different objects, organs, or regions of a patient may also be scanned. The MR data may be k-space data or image data. Image data may be MR data after Fourier transform into object space. The image data may be at any point after transform, so may be scalar values or may be formatted as RGB values for a display screen. MR data or image data may be scanning data to be used to generate an image on a display. MR data may be data being processed to generate an image, data formatted for display, or data that has been used to display. MR data may be data with no or some image processing. In an embodiment, the MR data may represent a volume. Three-dimensional datasets are obtained. As k-space data, information content may be provided that is responsive to a three-dimensional distribution of locations, but the data itself does not directly represent the locations prior to transform. In alternative embodiments, two-dimensional datasets representing or responsive to tissue in planes are obtained. In other embodiments, sequences of MR data responsive to the same tissue over time are acquired for training. Alternative methods may be used to acquire the MR data. The MR data may be acquired remotely from the server or workstation. The MR data may be stored locally onsite or offsite, for example in the cloud.

As used herein, MR data includes both raw MR data and processed MR data. Processed MR data may include image and volume data. MR data may include 2D images, sequences of 2D images, 3D volumetric imagery, or sequence of 3D volumetric imagery. If the MR data is defined in 3D space (e.g., obtained from a series of MR images), each image "slice" may be provided individually in a "slice-by-slice" manner. Alternatively, the MR data may be acquired as 3D volumetric data directly. The examples described herein use three-dimensional MR data referred to as volumes. Additionally, the terms MR data and volume may be used interchangeably in that the MR data represents at least one volume. Volumes are encoded using an array of elements referred to as voxels. A voxel represents a value on a regular or irregular grid in three-dimensional space. Two-dimensional MR data may be encoded using a bitmap of pixels.

In an embodiment, the system 100 is configured to analyze/interpret the MR data as the screening procedure proceeds. The system 100 may adjust an ongoing screening procedure based on real-time analysis of the real-time results of the whole body MRI screening. In an embodiment, the system 100 may identify and highlight areas of potential concern, such as tumors, vascular anomalies, or signs of degenerative diseases and adjust the set of sequences based thereon. In an embodiment, the system 100 may compare the current scans with prior MRIs, CTs, or other images from the patient's history, emphasizing any changes or developments. By adjusting the screening procedure in real time, the system 100 may remove unnecessary sequences or add in sequences so that the system 100 may provide a comprehensive report after the screening procedure ends.

As an example, abnormal regions are identified in MR data from an initial sequence (or other sequence). A global intensity distribution for a region of the scan may indicate whether there's a deviation from normal and where the deviation exists. The global intensity distribution may be analysis using one or more networks trained using deep learning techniques. In one implementation of analysis, the MR data is segmented and classified using one or more machine learning techniques, for example with an AI based model. The MR data may be segmented using any segmentation method. Segmentation is the process of dividing an input into different parts or sections, e.g. for medical imaging, delineating the boundaries, or contours, of various tissues or structures in the body. Segmentation may also include classification. Classification assigns a label to the MR data, e.g. normal or abnormal, level of severity, a diagnosis, or type of tissue. Classification may assign to each element in the image a tissue class when the classes are defined in advance. Classification of the tissue types requires segmentation of the MR data into different parts. Image segmentation can be performed on two dimensional images, sequences of two-dimensional images, three-dimensional volume, or sequences of three-dimensional volumes. If the data is defined in three-dimensional space (e.g., obtained from a series of MR images), each image slice may be segmented individually in a slice-by-slice manner. The two-dimensional slices are then connected into a 3D volume or a continuous surface.

The training data for the AI based models/networks may include ground truth data or gold standard data. Ground truth data and gold standard data is data that includes correct or reasonably accurate labels. For the segmentation problem, the training data includes the original data and associated segmented data. Labels for segmentation purposes include labels for each pixel/voxel in the segmented data. The segmented data may be generated and labeled using any method or process, for example, manually by an operator or automatically by one or more automatic methods. Different training data may be acquired for different segmentation tasks. For example, a first set of training data may be used to train a first network for segmenting the torso of the patient, while a second set of training data may be used to train a second network for segmenting a particular organ such as the liver or heart. The training data may be acquired at any point prior to inputting the training data into the trained network. The training data may include volumes of different resolutions or contrast. The training data may be updated after acquiring new data. The updated training data may be used to retrain or update the trained network. The output of the training process is a trained network that is configured to input MR data and output segmented and classified MR data. For the segmentation and classification, single or multiple networks may be trained and used. One network may be trained to perform the segmentation task while a second network may be trained to perform the tissue classification. Different networks for different tasks may use different training data. For example, networks (AI models) for segmentation may use different training data than networks (AI models) that are configured to select the sequences or interpret the data. An AI model that is used to selected the sequences may be trained on past procedure data including patient information, which sequences were performed, and whether an accurate or useful diagnosis was provided.

In an example, the output of the trained network for segmentation and tissue classification may be input into a second trained network that is configured for abnormality detection or other medical diagnosis. The second trained network may be trained using deep learning techniques to input a segmented/classified image and identify abnormal regions. One method of identifying abnormal regions is by using a trained autoencoder network. An autoencoder is a neural network that is trained by unsupervised learning. The autoencoder is trained to learn reconstructions that are close to its original input. An autoencoder is composed of two parts, an encoder and a decoder. The encoder compresses the input data into a latent space. The decoder decompresses the latent space in order to attempt to reconstruct the input data. During training, the output of the decoder is compared to the original input to calculate a reconstruction error. Using multiple repetitions and adjustments, the autoencoder learns to minimize the reconstruction error. The output of the training process is a trained autoencoder network.

In application, autoencoder-based anomaly detection is a deviation-based anomaly detection method. The autoencoder may be trained adversarially to distinguish healthy case from pathological cases. The autoencoder uses the reconstruction error on input data as an anomaly score. Data points with high reconstruction errors are considered to be anomalies. Only data with normal instances are used to train the autoencoder. After training, the autoencoder reconstructs normal data very well, while failing to do so with anomaly data, which the autoencoder has not encountered. The output of the autoencoder is anomaly data that describes one or more regions in the MR data that are unexpected. The abnormal regions provide guidance for further imaging protocols or sequences.

After anomalies are identified, the system 100 may adjust the set of sequences, for example to add or remove a sequence based on any detected anomaly. In an example, if there is an anomaly detected in a particular organ, the system 100 may automatically elect to perform a specific scan for the particular organ. Similarly, the system 100 may determine that a particular sequence or scan is not needed. In this way, by automatically acquiring the additional data during the whole body scan and not after, the system 100 is able to streamline the procedure so that the necessary data is acquired without performing unnecessary scans.

The networks described above for certain tasks may be specifically configured for each respective task. Different networks and configurations may be used. For example, a DenseNet or other network arrangements may also be used for the trained networks or other trained networks described above for segmentation, classification, or analysis. A DenseNet connects each layer in a network to every other layer in a feed-forward fashion. For each layer in the DenseNet, the feature-maps of all preceding layers are used as inputs, and the output feature-map of that layer is used as input into all subsequent layers. In the DenseNet, for each layer, the feature maps of all preceding layers are used as inputs, and its own feature maps are used as inputs into all subsequent layers. To reduce the size of the network, the DenseNet may include transition layers. The layers include convolution followed by average pooling. The transition layers reduce height and width dimensions but leave the feature dimension the same. The neural network may further be configured as a U-net. The U-Net is an autoencoder in which the outputs from the encoder-half of the network are concatenated with the mirrored counterparts in the decoder-half of the network. Skip connections prevent the middle of the network from becoming a bottleneck.

Other deep architectures that may be used include convolutional neural network (CNN) or deep belief nets (DBN), but other deep networks may be used. CNN learns feed-forward mapping functions while DBN learns a generative model of data. In addition, CNN uses shared weights for all local regions while DBN is a fully connected network (e.g., including different weights for all regions of an image). The training of CNN is entirely discriminative through back-propagation. DBN, on the other hand, employs the layer-wise unsupervised training (e.g., pre-training) followed by the discriminative refinement with back-propagation if necessary. In an embodiment, the arrangement of the trained network is a fully convolutional network (FCN). Alternative network arrangements may be used, for example, a 3D Very Deep Convolutional Networks (3D-VGGNet). VGGNet stacks many layer blocks containing narrow convolutional layers followed by max pooling layers. A 3D Deep Residual Networks (3D-ResNet) architecture may be used. A Resnet uses residual blocks and skip connections to learn residual mapping.

Each of the trained networks are defined as a plurality of sequential feature units or layers. Sequential is used to indicate the general flow of output feature values from one layer to input to a next layer. The information from the next layer is fed to a next layer, and so on until the final output. The layers may only feed forward or may be bi-directional, including some feedback to a previous layer. The nodes of each layer or unit may connect with all or only a sub-set of nodes of a previous and/or subsequent layer or unit. Skip connections may be used, such as a layer outputting to the sequentially next layer as well as other layers. Rather than pre-programming the features and trying to relate the features to attributes, the deep architecture is defined to learn the features at different levels of abstraction based on an input MR data with or without pre-processing. The features are learned to reconstruct lower level features (i.e., features at a more abstract or compressed level). For example, features for reconstructing an image are learned. For a next unit, features for reconstructing the features of the previous unit are learned, providing more abstraction. Each node of the unit represents a feature. Different units are provided for learning different features.

Various units or layers may be used, such as convolutional, pooling (e.g., max-pooling), deconvolutional, fully connected, or other types of layers. Within a unit or layer, any number of nodes is provided. For example, 100 nodes are provided. Later or subsequent units may have more, fewer, or the same number of nodes. In general, for convolution, subsequent units have more abstraction. For example, the first unit provides features from the image, such as one node or feature being a line found in the image. The next unit combines lines, so that one of the nodes is a corner. The next unit may combine features (e.g., the corner and length of lines) from a previous unit so that the node provides a shape indication. For transposed-convolution to reconstruct, the level of abstraction reverses. Each unit or layer reduces the level of abstraction or compression.

In another embodiment, supervised learning may be used with direct classification of the findings into selecting the next sequences. Findings are reported from each sequence and therefore specific action(s) can be taken in accordance to the finding and sequence. Matching a diagnosis to the needed sequence may also be done by an AI based model that is based on the findings from each sequence. After the addition acquisition sequences are determined, the one or more acquisition sequences are performed and the results may be automatically interpreted.

Referring back to FIG. 4, at act A130, the system 100 interprets the results of the whole body MRI screening. During and after the whole body MRI screening, the system 100 is configured using AI algorithms and/or models to identify and highlight areas of potential concern, such as tumors, vascular anomalies, or signs of degenerative diseases. The system 100 is configured to compare the current scans with prior MRIs, CTs, or other images from the patient's history, emphasizing any changes or developments. The system 100 is further configured to provide predictive insights. By integrating the MRI data with broader medical databases and the patient's medical history, the system 100 using AI can suggest potential risks or future complications. In addition, the system 100 is configured to generate preliminary reports, integrating its findings in a structured and easy-to-understand format, and speeding up the review process for radiologists. Besides reports dedicated to a radiologist the system 100 can generate reports that are dedicated for patients/consumers with simpler language and visuals.

In an example, the system 100 may use an AI based model to evaluate the iron and fat content of the liver in order to monitor the early stages of liver diseases. This analysis uses a fat and iron screening part (First look Dixon), plus two methods for evaluation, HISTO (voxel based) and Multi-echo Dixon VIBE (image based), and provides a clinical report. In another example, the system 100 may use an AI based model to determine the ventricular function of a patient. During a scan, the heart is located and the endo- and epicardial borders are detected automatically. Data output is right after the image reconstruction without any user interaction. The data may be used to provide reliable and fast cardiac volumetric and ejection fraction assessment in a busy, throughput oriented environment and Automatic volumetric assessment and ejection fraction calculation in cardiomyopathy (dilated, hypertrophic, etc.), pericardial disease, cardiac tumors and cardiac transplants. In another example, the system 100 may use a convolutional image-to-image deep learning pipeline for performing classification without fully connected layers as in conventional classification pipelines. The same network may also be used for localization of suspicious regions by examining the responses across different channels. In another example, the system 100 may use the data from one or more of the sequences to automatically evaluate evaluation of metastases in patients. Different cancers such as hematological cancer, prostate cancer, melanoma, breast cancer, and lymphoma among others.

Figure 5:
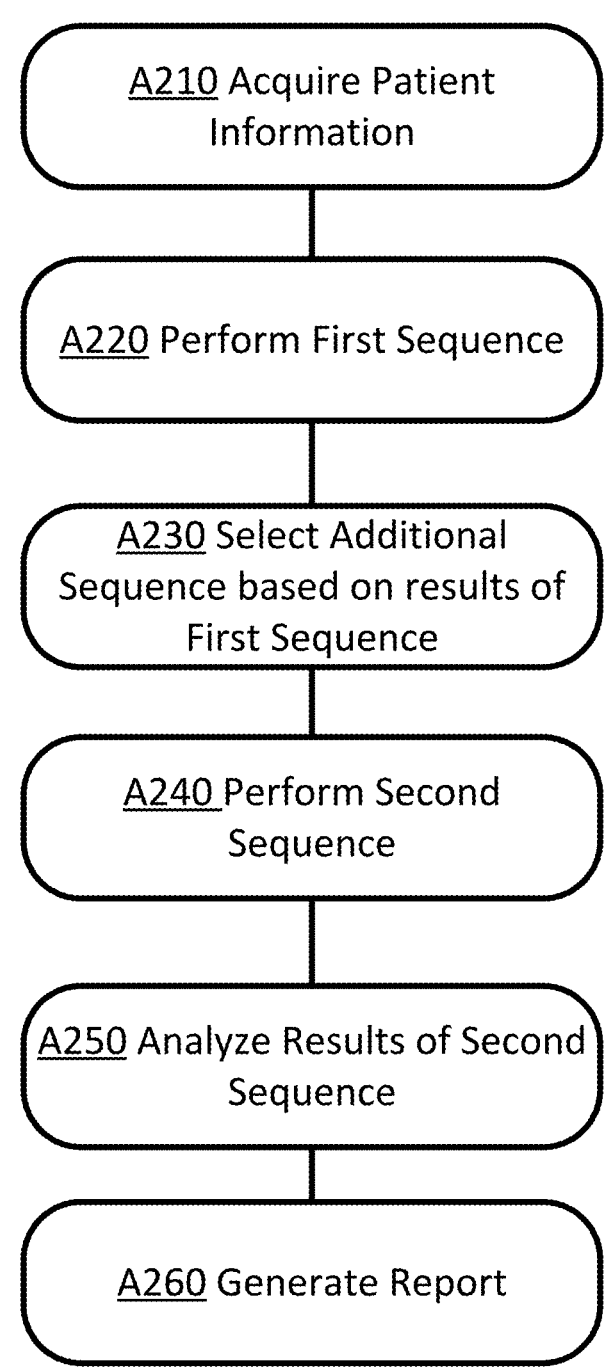
FIG. 5 depicts a method for Whole Body MRI screening according to an embodiment.

FIG. 5 depicts an example of the application of the Whole Body MRI screening using AI powered models. At act A210, patient information is acquired and input into an AI model configured to output a plurality of sequences for a personalized Whole Body MRI Screening tailored to the patient. A "core protocol" for WB-MRI may be selected, for example, composed of T1 weighted GRE sequences together with T2 weighted TSE sequences and DWI. Anatomical coverage, field of view and slice thickness may be homogeneous across the sequences, in order to facilitate image correlation and interpretation. If the patient's history or information indicates a particular proclivity to a disease or cancer, an additional specific sequence may be selected by the AI model.

At act A220, a first sequence of the plurality of sequences is performed by an MR scanning system 36. The first sequence, may for example, be a low resolution scan of the entire body of the patient. The results of the first sequence are analyzed and interpreted by at least one AI based model. The large number of images produced in each WB-MRI examination complicates extracting the quantitative information provided. This necessitates considerable time for reading and reporting, and can increase the risk of misinterpretations. Semi-automatic or automatic segmentation techniques may be used to distinguish malignant lesions from healthy tissue and benign findings.

At act A230, an additional sequence is added to the plurality of sequences based on an anomaly detected in the data from the first sequence. The additional sequence may, for example, be provided to acquire particular information relating to the anomaly. The additional sequence, for example may include sagittal imaging of the whole spine, dedicated brain imaging, MRI mammography, coverage of the lower limbs, etc. At act A240, the additional sequence is performed by the MR scanning system 36. The results of the additional sequence are analyzed and interpreted by at least one AI based model.

At act A250, the further sequences of the plurality of sequences are analyzed and interpreted in real time. If any further additional sequences are required, the system 100 may select and perform such a further additional sequence. By performing analysis and real time interpretation, the system 100 is able to acquire all of the data that would be useful in a single session. At act A260, the system 100 analyses and interprets the entirety of the data from the plurality of initial sequences and any additional sequences.

At act A270, the system 100 generates a diagnostic report based on the analysis and interpterion of the data.

While the invention has been described above by reference to various embodiments, many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

The following is a list of non-limiting illustrative embodiments disclosed herein:

Illustrative embodiment 1. A method for Whole Body MRI Screening using AI powered models, the method comprising: determining, by a first AI model, a personalized set of MR sequences for a patient based on initial images and available clinical data; performing whole body MRI screening for the patient comprising the personalized set of MR sequences; and interpreting the results of the whole body MRI screening using one or more second AI models.

Illustrative embodiment 2: The method of Illustrative embodiment 1, wherein determining comprises: tailoring the personalized set of MR sequences based on the patent's age, risk factors, and prior medical history.

Illustrative embodiment 3: The method of Illustrative embodiment 1, further comprising: adjusting the whole body MRI screening based on real-time analysis of real-time results of one or more of the personalized set of MR sequences.

Illustrative embodiment 4. The method of Illustrative embodiment 1, wherein interpreting comprises: identifying one or more areas of potential concern for the patient, wherein the one or more areas related to a tumor, vascular anomaly, or sign of degenerative diseases.

Illustrative embodiment 5. The method of Illustrative embodiment 1, further comprising: identifying one or more areas of potential concern for the patient based on results from an initial sequence of the personalized set of MR sequences, wherein the one or more areas related to a tumor, vascular anomaly, or sign of degenerative diseases; and selecting a new sequence not included in the personalized set of MR sequences based on the identification.

Illustrative embodiment 6. The method of Illustrative embodiment 1, wherein interpreting comprises: comparing results of the personalized set of MR sequences with prior MRIs, CTs, or other images from the patient's history; and identifying any changes or developments.

Illustrative embodiment 7. The method of Illustrative embodiment 6, wherein comparing is performed using an autoencoder-based anomaly detection method.

Illustrative embodiment 8. The method of Illustrative embodiment 1, further comprising: generating a report based on the interpreted results.

Illustrative embodiment 9. The method of Illustrative embodiment 8, wherein the report includes simple language and simple visuals for the patient.

Illustrative embodiment 10. The method of Illustrative embodiment 1, wherein the first AI model and/or the one or more second AI models comprise machine trained neural networks.

Illustrative embodiment 11. The method of Illustrative embodiment 1, wherein the one or more second AI models comprise at least one machine trained network trained for segmenting image data for a specific region of the patient.

Illustrative embodiment 12. The method of Illustrative embodiment 11, wherein the at least one machine trained network comprises a machine trained segmentation network.

Illustrative embodiment 13. A system for whole body MR screening, the system comprising: a first AI model configured to select a personalized set of MR sequences for a patient based on initial images and available clinical data; a MR scanner configured to perform the personalized set of MR sequences; a second AI model configured to analyze data from a first sequence of the personalized set of MR sequences; and a third AI model configured to interpret the analysis of the second AI model and generate a diagnostic report.

Illustrative embodiment 14. The system of Illustrative embodiment 13, wherein the first AI model is configured to tailor the personalized set of MR sequences based on the patent's age, risk factors, and prior medical history.

Illustrative embodiment 15. The system of Illustrative embodiment 13, wherein the personalized set of MR sequences are adjusted based on the analysis of the second AI model.

Illustrative embodiment 16. The system of Illustrative embodiment 13, wherein the second AI model is configured to identify one or more areas of potential concern for the patient, wherein the one or more areas related to a tumor, vascular anomaly, or sign of degenerative diseases.

Illustrative embodiment 17. The system of Illustrative embodiment 13, further comprising: a fourth AI model configured to analyze data from a second sequence of the personalized set of MR sequences, wherein the third AI model is further configured to interpret the analysis of the fourth AI model and generate the diagnostic report based at least partially thereon.

Illustrative embodiment 18. The system of Illustrative embodiment 13, wherein the third AI model is configured to compare results of the personalized set of MR sequences with prior MRIs, CTs, or other images from the patient's history to generate the diagnostic report.

Illustrative embodiment 19. The system of Illustrative embodiment 13, wherein the first AI model, second AI model, and third AI model comprise machine trained neural networks configured for each respective task.

Illustrative embodiment 20. A method for whole body MR screening, the method comprising: determining, by a first AI model, a personalized set of MR sequences for a patient based on initial images and available clinical data; performing, by a MR scanning system, a first sequence of the personalized set of MR sequences; analyzing, by a second AI model, results from the first sequence, wherein analyzing comprises at least identifying an anomaly in the results; selecting, by a third AI model, an additional sequence to be performed based on the analysis of the second AI model; performing, by the MR scanning system, the additional sequence; interpreting, by a fourth AI model, the results of the additional sequence; and generating, by a fifth AI model, a report based on at least the results of the additional sequence.

The invention claimed is:

1. A method for Whole Body MRI Screening using AI powered models, the method comprising:

determining, by a first AI model, a personalized set of MR sequences for a single-session whole body MRI screening spanning from at least a patient's head to pelvis, wherein the personalized set of MR sequences is tailored for the patient based on at least one of the patient's age or prior medical history in addition to initial images and available clinical data;

performing the single-session whole body MRI screening for the patient comprising the personalized set of MR sequences; and identifying, using one or more second AI models, one or more abnormal regions for the patient based on results of the single-session whole body MRI screening.

2. The method of claim 1, further comprising:

adjusting the whole body MRI screening based on real-time analysis, by the one or more second AI models, of real-time results of one or more of the personalized set of MR sequences.

3. The method of claim 1, further comprising:

identifying the one or more abnormal regions for the patient based on results from an initial sequence of the personalized set of MR sequences; and selecting a new sequence not included in the personalized set of MR sequences based on the identification.

4. The method of claim 1, further comprising:

comparing results of the single-session whole body MRI screening with prior MRIs, CTs, or other images from the patient's history; and identifying any changes or developments.

5. The method of claim 4, wherein comparing is performed using an autoencoder-based anomaly detection method.

6. The method of claim 1, further comprising:

generating a report based on the interpreted results.

7. The method of claim 1, wherein the first AI model and/or the one or more second AI models comprise machine trained neural networks.

8. The method of claim 1, wherein the one or more second AI models comprise at least one machine trained network trained for segmenting image data for a specific region of the patient.

9. The method of claim 8, wherein the at least one machine trained network comprises a machine trained segmentation network.

* * * * *